(12) United States Patent
Zhang (10) Patent No.: US 10,945,602 B2
(45) Date of Patent: Mar. 16, 2021

(54) MONITORING PARAMETER THRESHOLD VALUE SETTING METHOD AND MONITORING SYSTEM

(71) Applicant: SHENZHEN MINDRAY BIO-MEDICAL ELECTRONICS CO., LTD., Shenzhen (CN)

(72) Inventor: Jianhui Zhang, Shenzhen (CN)

(73) Assignees: SHENZHEN MINDRAY BIO-MEDICAL ELECTRONICS CO., LTD., Shenzhen (CN); SHENZHEN MINDRAY SCIENTIFIC CO., LTD., Shenzhen (CL)

( * ) Notice: Subject to any disclaimer, the term of this patent is extended or adjusted under 35 U.S.C. 154(b) by 151 days.

(21) Appl. No.: 15/934,313

(22) Filed: Mar. 23, 2018

(65) Prior Publication Data

US 2018/0206721 A1    Jul. 26, 2018

Related U.S. Application Data

(63) Continuation of application No. PCT/CN2015/090927, filed on Sep. 28, 2015.

(51) Int. Cl.
*A61B 5/00* (2006.01)
*A61B 5/021* (2006.01)
(Continued)

(52) U.S. Cl.
CPC ............ *A61B 5/0006* (2013.01); *A61B 5/021* (2013.01); *A61B 5/02455* (2013.01);
(Continued)

(58) Field of Classification Search
CPC . A61B 5/0006; A61B 5/02455; A61B 5/0402; A61B 5/743; A61B 5/7435; A61B 5/021; A61B 5/746
See application file for complete search history.

(56) References Cited

U.S. PATENT DOCUMENTS 9,993,164 B2 * 6/2018 Tanishima ............ A61B 5/0205
2007/0208244 A1 * 9/2007 Brauker ............. A61B 5/14865
600/365
(Continued)

FOREIGN PATENT DOCUMENTS

| CN | 103040460 | 4/2013 |
|----|-----------|--------|
| CN | 103648372 | 3/2014 |
| JP | 4365020   | 8/2009 |

*Primary Examiner* — Eric D. Bertram
(74) *Attorney, Agent, or Firm* — Kory D. Christensen (57) ABSTRACT

The embodiment of the present disclosure discloses a monitoring parameter threshold value setting method, comprising the following steps: selecting at least one threshold value indicator of the monitoring parameter that needs a threshold value setting; forming and displaying a corresponding threshold value setting graphic according to the said threshold value indicator, wherein, in the said threshold value setting graphic, said threshold value indicator corresponds to an indication icon; responding to the threshold value setting of the threshold value indicator by a user, and adjusting the indication icon corresponding to the threshold value indicator to the corresponding position of the said indicating graphic. The embodiment of the present application also discloses a monitoring system provided with the said monitoring parameter threshold value setting method, which can provide a graphical indication when a user sets a threshold value of the monitoring parameter, thereby improving the convenience and accuracy of the threshold value setting.

20 Claims, 8 Drawing Sheets

(51) Int. Cl.
  *A61B 5/0245*    (2006.01)
  *A61B 5/318*     (2021.01)
  *A61B 5/363*     (2021.01)

(52) U.S. Cl.
  CPC .............. *A61B 5/318* (2021.01); *A61B 5/363* (2021.01); *A61B 5/743* (2013.01); *A61B 5/746* (2013.01); *A61B 5/7435* (2013.01)

(56) References Cited

U.S. PATENT DOCUMENTS

| | | | |
|---|---|---|---|
| 2012/0143067 A1 | 6/2012 | Watson et al. | |
| 2013/0044111 A1* | 2/2013 | VanGilder | A61B 5/044 345/440 |
| 2014/0012096 A1* | 1/2014 | Nomura | A61B 5/742 600/301 |
| 2014/0088392 A1* | 3/2014 | Bernstein | G16H 50/20 600/365 |
| 2016/0374580 A1* | 12/2016 | Vainoras | A61B 5/7275 600/509 |

* cited by examiner

MONITORING PARAMETER THRESHOLD VALUE SETTING METHOD AND MONITORING SYSTEM

CROSS-REFERENCE TO RELATED APPLICATIONS

This application is a continuation of PCT Application No. PCT/CN2015/090927, filed Sep. 28, 2015, for "MONITORING PARAMETER THRESHOLD VALUE SETTING METHOD AND MONITORING SYSTEM," which is incorporated herein by reference.

TECHNICAL FIELD

The present disclosure relates to the medical field and in particular to a monitoring parameter threshold setting method and a monitoring system.

BACKGROUND

Conventionally, patient monitors involve various threshold settings, such as setting an alarm threshold for a certain monitoring parameter. It is relatively simple to set a threshold for a single monitoring parameter in order to determine whether a measured value is too low or too high, in which case it is only necessary to provide a simple threshold setting input region next to a parameter displayed in text on a setting page, such that a user can input a desired threshold (numerical value) therein. However, some monitoring parameters have numerous threshold indicators and threshold settings for some monitoring parameters may be interrelated. For example, where a parameter is delimited by a single threshold, values exceeding the threshold being regarded as abnormal, and values below the threshold being normal, this parameter can be said to have only one threshold indicator. Alternatively, where three states, i.e. high, medium and low states, are defined for a parameter by two different thresholds, this parameter can be said to have two threshold indicators, i.e. an upper threshold indicator and a lower threshold indicator. In some cases, in order to determine a special condition of a patient, threshold indicators of two or more parameters need to be combined for joint determination. In these cases, it is difficult for a user to determine the relationship between various threshold settings from existing threshold interfaces. Therefore, the user (such as a nurse) needs to completely rely on associative memory and experience to perform threshold setting for the monitoring parameters, so that it can be particularly complicated to set multiple associated monitoring thresholds, for example, and inaccurate settings occur frequently.

SUMMARY

A technical problem to be solved in embodiments of the present disclosure is to provide a monitoring parameter threshold setting method and a monitoring system. When a user sets a threshold of a monitoring parameter, graphical indications can be provided to improve the convenience or accuracy of threshold setting.

To resolve the above technical problem, one aspect of the embodiments of the present disclosure provides a monitoring parameter threshold setting method including the following steps: selecting at least one threshold indicator that is of a monitoring parameter and for which a threshold needs to be set; forming and displaying a threshold setting indication graph according to the at least one threshold indicator of the monitoring parameter, wherein the threshold indicator corresponds to an indication icon in the threshold setting indication graph; and in response to a threshold value of the threshold indicator set by a user, adjusting the indication icon corresponding to the threshold indicator in the threshold setting indication graph to a corresponding position.

The adjusting step may further include: determining a threshold indicator of the monitoring parameter that is currently operated by the user, and an indication icon corresponding to the threshold indicator; obtaining a latest position of the indication icon corresponding to the threshold indicator according to a latest threshold value set by the user for the threshold indicator; and adjusting the indication icon to the latest position in the threshold setting indication graph.

In one embodiment, the adjusting step may include: determining a threshold indicator of the monitoring parameter that is currently operated by the user, and an indication icon corresponding to the threshold indicator; highlighting the indication icon corresponding to the threshold indicator operated by the user in the threshold setting indication graph; obtaining a latest position of the indication icon corresponding to the threshold indicator according to a latest threshold value set by the user for the threshold indicator of the monitoring parameter; and dynamically moving the indication icon from a current position to the latest position in the threshold setting indication graph.

The highlighting step may further include highlighting the indication icon by flickering, color changing, or thickness changing.

The step of forming and displaying a threshold setting indication graph may include: when two or more measurement units correspond to the at least one threshold indicator of the monitoring parameter, forming and displaying a two-dimensional threshold setting indication graph according to an association relationship of the at least one threshold indicator of the monitoring parameter, wherein one of the measurement units is selected as an ordinate and a maximum value of the ordinate is determined, and another one of the measurement units is selected as an abscissa and a maximum value of the abscissa is determined; and an indication icon corresponding to each threshold indicator of the monitoring parameter is a segment parallel to the abscissa or the ordinate, and the at least one segment divides a region jointly enclosed by the abscissa, an abscissa maximum value line, the ordinate, and an ordinate maximum value line, and expected analysis result information is displayed in each small region obtained after division.

The threshold indicator of the monitoring parameter may include the following: the monitoring parameter includes PVCs and a heart rate, the PVCs correspond to two threshold indicators: ventricular tachycardia PVCs and ventricular bradycardia PVCs, and the heart rate corresponds to two threshold indicators: a ventricular tachycardia heart rate and a ventricular bradycardia heart rate, wherein a PVCs measurement unit is selected as the abscissa and a heart rate measurement unit is selected as the ordinate.

An indication icon corresponding to the ventricular tachycardia PVCs is a first adjustable segment parallel to the ordinate, an indication icon corresponding to the ventricular bradycardia PVCs is a second adjustable segment parallel to the ordinate, and the first adjustable segment and the second adjustable segment are parallel to each other; an indication icon corresponding to the ventricular tachycardia heart rate is a third adjustable segment parallel to the abscissa, an indication icon corresponding to the ventricular bradycardia heart rate is a fourth adjustable segment parallel to the abscissa, and the third adjustable segment and the fourth adjustable segment are parallel to each other.

The step of forming and displaying a threshold setting indication graph may include: when one measurement unit corresponds to the at least one threshold indicator of the monitoring parameter, forming and displaying a two-dimensional threshold setting indication graph according to an association relationship of the at least one threshold indicator of the monitoring parameter, wherein the measurement unit is selected as an ordinate, and a maximum value of the ordinate is determined; and an indication icon corresponding to a threshold of the threshold indicator of the monitoring parameter is a segment parallel to the abscissa, and the at least one segment divides a region jointly enclosed by the ordinate or a line parallel to the ordinate, an ordinate maximum value line or a line parallel to the ordinate maximum value line, and the abscissa, and expected analysis result information is displayed in each small region obtained after division.

The threshold indicator of the monitoring parameter includes: a maximum value of diastolic pressure, a minimum value of diastolic pressure, a maximum value of systolic pressure, and a minimum value of systolic pressure, where a measurement unit of the maximum value of diastolic pressure is selected as the ordinate.

Another aspect of the embodiments of the present disclosure further provides a monitoring system, comprising: a monitoring unit, configured to obtain a monitoring parameter of a patient; a selection unit, configured to allow a user to select at least one threshold indicator that is of a monitoring parameter and for which a threshold needs to be set; a threshold setting indication graph display unit, configured to form and display a threshold setting indication graph according to the threshold indicator, wherein the threshold indicator corresponds to an indication icon in the threshold setting indication graph; and an adjustment unit, configured to adjust the indication icon corresponding to the threshold indicator in the threshold setting indication graph to a corresponding position in response to a threshold value of the threshold indicator set by a user.

The adjustment unit may further include: a determining subunit, configured to determine a threshold indicator of the monitoring parameter that is currently operated by the user, and an indication icon corresponding to the threshold indicator of the monitoring parameter; a latest position obtaining unit, configured to obtain a latest position of the indication icon corresponding to the threshold indicator according to a latest threshold value set by the user for the threshold indicator; and an indication icon display unit, configured to adjust the indication icon to the latest position in the threshold setting indication graph.

The adjustment unit may further include: a determining subunit, configured to determine a threshold indicator of the monitoring parameter that is currently operated by the user, and an indication icon corresponding to the threshold indicator; a highlight subunit, configured to highlight the indication icon corresponding to the threshold indicator operated by the user in the threshold setting indication graph; a latest position obtaining unit, configured to obtain a latest position of the indication icon corresponding to the threshold indicator according to a latest threshold value set by the user for the threshold indicator; and a dynamic movement unit, configured to dynamically move the indication icon from a current position to the latest position in the threshold setting indication graph.

The highlight subunit may highlight the indication icon by flickering, color changing, or thickness changing.

The threshold setting indication graph display unit may be further configured to: when two or more measurement units correspond to the at least one threshold indicator of the monitoring parameter, form and display a two-dimensional threshold setting indication graph according to an association relationship of the at least one threshold indicator of the monitoring parameter, wherein one of the measurement units is selected as an ordinate and a maximum value of the ordinate is determined, and another one of the measurement units is selected as an abscissa and a maximum value of the abscissa is determined; and an indication icon corresponding to each threshold indicator of the monitoring parameter is a segment parallel to the abscissa or the ordinate, and the at least one segment divides a region jointly enclosed by the abscissa, an abscissa maximum value line, the ordinate, and an ordinate maximum value line, and expected analysis result information is displayed in each small region obtained after division.

The monitoring parameter may include PVCs and a heart rate, the PVCs correspond to two threshold indicators: ventricular tachycardia PVCs and ventricular bradycardia PVCs, and the heart rate corresponds to two threshold indicators: a ventricular tachycardia heart rate and a ventricular bradycardia heart rate, wherein a PVCs measurement unit is selected as the abscissa and a heart rate measurement unit is selected as the ordinate.

An indication icon corresponding to the ventricular tachycardia PVCs is a first adjustable segment parallel to the ordinate, an indication icon corresponding to the ventricular bradycardia PVCs is a second adjustable segment parallel to the ordinate, and the first adjustable segment and the second adjustable segment are parallel to each other; an indication icon corresponding to the ventricular tachycardia heart rate is a third adjustable segment parallel to the abscissa, an indication icon corresponding to the ventricular bradycardia heart rate is a fourth adjustable segment parallel to the abscissa, and the third adjustable segment and the fourth adjustable segment are parallel to each other.

The threshold setting indication graph display unit may be further configured to: when one measurement unit corresponds to the at least one threshold indicator of the monitoring parameter, forming and displaying a two-dimensional threshold setting indication graph according to an association relationship of the at least one threshold indicator of the monitoring parameter, wherein the measurement unit is selected as an ordinate, and a maximum value of the ordinate is determined; and an indication icon corresponding to a threshold of the threshold indicator of the monitoring parameter is a segment parallel to the abscissa, and the at least one segment divides a region jointly enclosed by the ordinate or a line parallel to the ordinate, an ordinate maximum value line or a line parallel to the ordinate maximum value line, and the abscissa, and expected analysis result information is displayed in each small region obtained after division.

The threshold indicator of the monitoring parameter includes: a maximum value of diastolic pressure, a minimum value of diastolic pressure, a maximum value of systolic pressure, and a minimum value of systolic pressure, where a measurement unit of the maximum value of diastolic pressure is selected as the ordinate.

By implementing the embodiments of the present disclosure, the following beneficial effects can be achieved. When a user sets a threshold of at least one threshold indicator of a monitoring parameter, a preset threshold setting indication graph can be used to indicate a relationship between thresholds of the threshold indicators of the monitoring parameter.

Furthermore, a threshold indicator of the monitoring parameter that is being set is highlighted, different from the other threshold indicators of the monitoring parameter.

Moreover, when a threshold value of a threshold indicator of the monitoring parameter is adjusted, a graphical change corresponding to the threshold of the threshold indicator of the monitoring parameter is displayed in the threshold setting indication graph.

Therefore, by implementing the embodiments of the present disclosure, when a user sets a threshold of a monitoring parameter, graphical indications can be realized, so as to improve the accuracy of the threshold setting.

DETAILED DESCRIPTION

The technical solutions of the embodiments of the present disclosure will be described below clearly and comprehensively in conjunction with the drawings. The embodiments described are merely some embodiments of the present disclosure and are not all of the possible embodiments. Based on the embodiments given in the present disclosure, all other embodiments that would be obtained by those of ordinary skill in the art without expending inventive effort shall fall within the scope of protection of the present disclosure.

Figure 1:
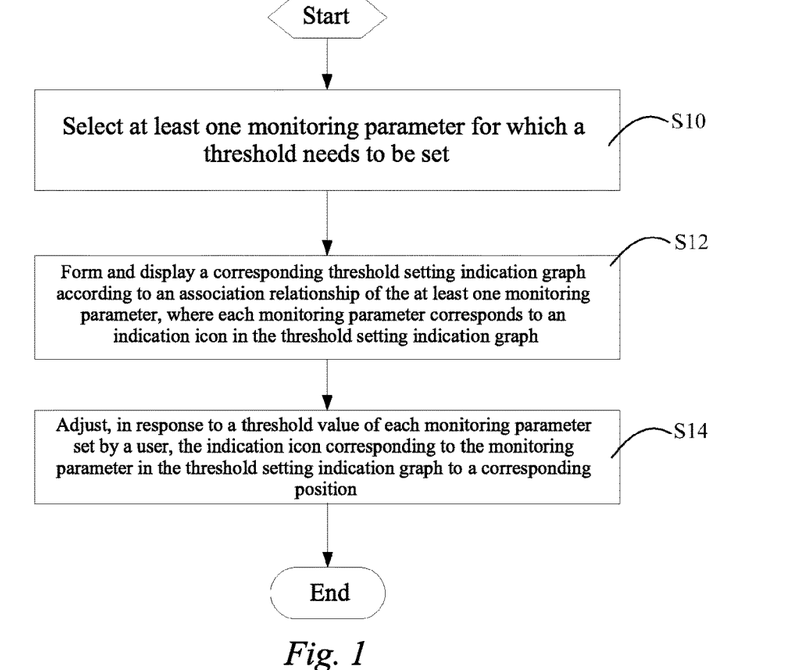
FIG. 1 is a main flow chart of an embodiment of a monitoring parameter threshold setting method provided by the present disclosure.

FIG. 1 shows a monitoring parameter threshold setting method according to the present disclosure. In this embodiment, when a user sets a threshold of a monitoring parameter of a monitor, graphical indications are used to prompt the user. The method may include the following steps:

Step S10: Select at least one threshold indicator that is of a monitoring parameter and for which a threshold needs to be set. Generally, the at least one threshold indicator of the monitoring parameter is in a linked relationship. For example, in some cases, values of two threshold indicators of the parameter may define an alarm region or result in a status determination.

Step S12: Form and display a corresponding threshold setting indication graph according to the at least one threshold indicator of the monitoring parameter, where each threshold indicator of the monitoring parameter corresponds to an indication icon in the threshold setting indication graph.

Step S14: In response to setting a threshold value of each threshold indicator of the monitoring parameter by a user, adjust the indication icon corresponding to the threshold indicator of the monitoring parameter in the threshold setting indication graph to a corresponding position.

As an example, step S12 may include:

if two or more measurement units correspond to the at least one threshold indicator of the monitoring parameter, forming and displaying a two-dimensional threshold setting indication graph according to an association relationship of the at least one threshold indicator of the monitoring parameter, where one of the measurement units is selected as an ordinate and a maximum value of the ordinate is determined, and another one of the measurement units is selected as an abscissa and a maximum value of the abscissa is determined; and the indication icon corresponding to each threshold indicator of the monitoring parameter is a segment parallel to the abscissa or the ordinate, and the at least one segment divides a region enclosed by the abscissa, an abscissa maximum value line, the ordinate, and an ordinate maximum value line, and expected analysis result information is displayed in each region obtained after division.

In this example, the threshold indicator of the monitoring parameters may include: a ventricular tachycardia PVCs threshold, a ventricular bradycardia PVCs threshold, a ventricular tachycardia heart rate threshold, and a ventricular bradycardia heart rate threshold, and a measurement unit of the ventricular tachycardia PVCs threshold may be selected as the abscissa, and a measurement unit of the ventricular tachycardia heart rate threshold may be selected as the ordinate.

In another example, step S12 may include:

if one measurement unit corresponds to the at least one threshold indicator of the monitoring parameter, forming and displaying a two-dimensional threshold setting indication graph according to an association relationship of the at least one threshold indicator of the monitoring parameter, where the measurement unit corresponding to the threshold indicator of the monitoring parameter is selected as an ordinate, and a maximum value of the ordinate is determined; and an indication icon corresponding to a threshold of the threshold indicator of the monitoring parameter is a segment parallel to an abscissa, and the at least one segment divides a region jointly enclosed by the ordinate or a line parallel to the ordinate, an ordinate maximum value line or a line parallel to the ordinate maximum value line, and the abscissa, and expected analysis result information is displayed in each small region obtained after division.

In this example, the threshold indicator of the monitoring parameter may include: a maximum value of diastolic pressure, a minimum value of diastolic pressure, a maximum value of systolic pressure, and a minimum value of systolic pressure, where a measurement unit of the maximum value of diastolic pressure may be selected as the ordinate.

Figure 2:
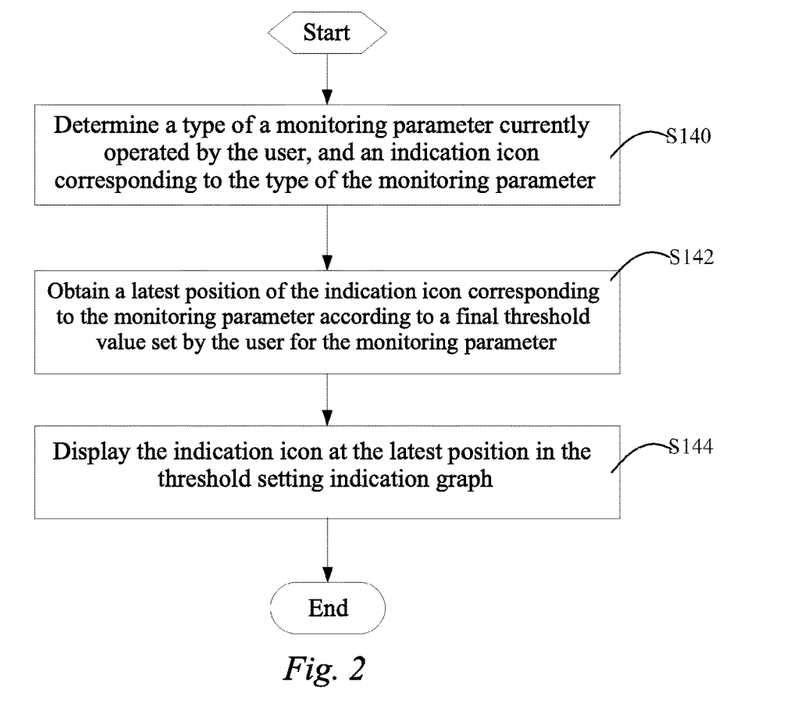
FIG. 2 is a detailed flow chart of an embodiment of step S14 in FIG. 1.

Referring to FIG. 2, a detailed flow chart of an embodiment of step S14 in FIG. 1 is shown. In this embodiment, step S14 includes:

Step S140: Determine a threshold indicator of the monitoring parameter that is currently operated by the user, and an indication icon corresponding to the threshold indicator of the monitoring parameter.

Step S142: Obtain a latest position of the indication icon corresponding to the threshold indicator of the monitoring parameter according to a latest threshold value set by the user for the threshold indicator of the monitoring parameter.

Step S144: Display the indication icon at the latest position in the threshold setting indication graph.

Figure 3:
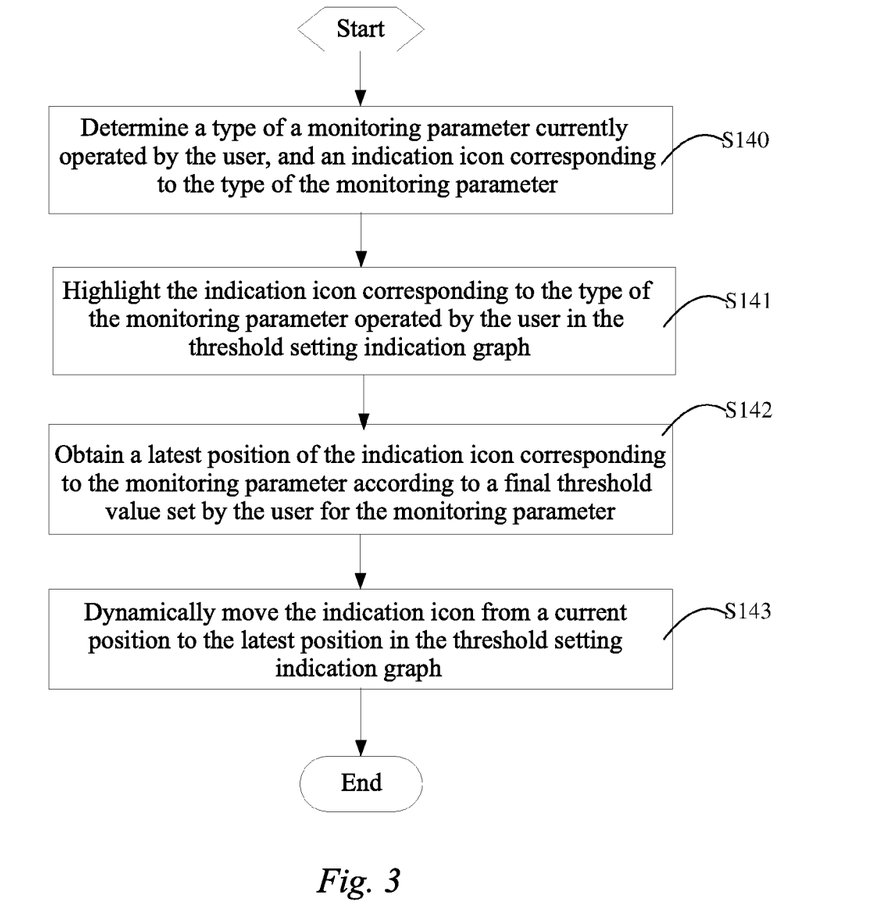
FIG. 3 is a detailed flow chart of another embodiment of step S14 in FIG. 1.

Referring to FIG. 3, a detailed flow chart in another embodiment of step S14 in FIG. 1 is shown. In this embodiment, step S14 includes:

Step S140: Determine a threshold indicator of the monitoring parameter that is currently operated by the user, and an indication icon corresponding to the threshold indicator of the monitoring parameter.

Step S141: Highlight the indication icon corresponding to the threshold indicator of the monitoring parameter operated by the user in the threshold setting indication graph. In specific embodiments, the indicator icon may be highlighted by flickering, color changing, or thickness changing.

Step S142: Obtain a latest position of the indication icon corresponding to the threshold indicator of the monitoring parameter according to a latest threshold value set by the user for the threshold indicator of the monitoring parameter.

Step S143: Dynamically move the indication icon from a current position to the latest position in the threshold setting indication graph.

For the convenience of understanding the technical solution of the present disclosure, two specific application examples are described below.

Figure 4:
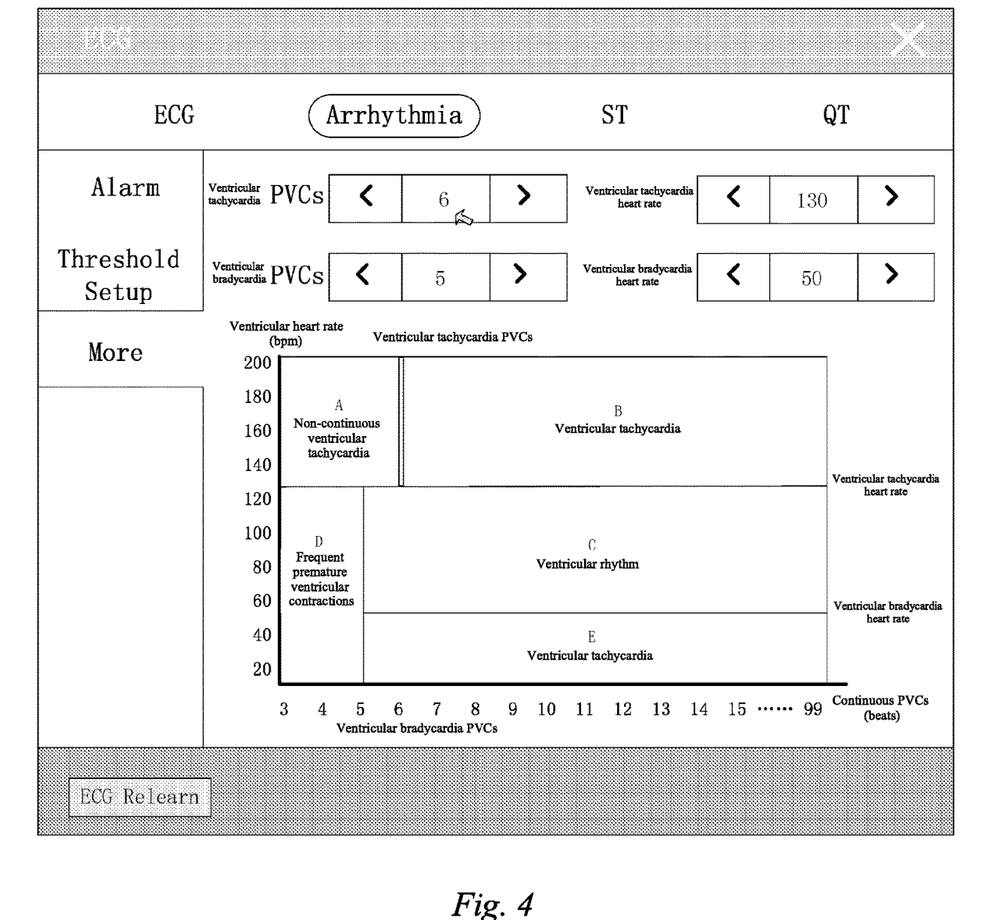
FIG. 4 is a schematic diagram of an interface for setting thresholds of arrhythmia-related monitoring parameters to which a monitoring parameter threshold setting method provided by the present disclosure is applied.
Figure 5:
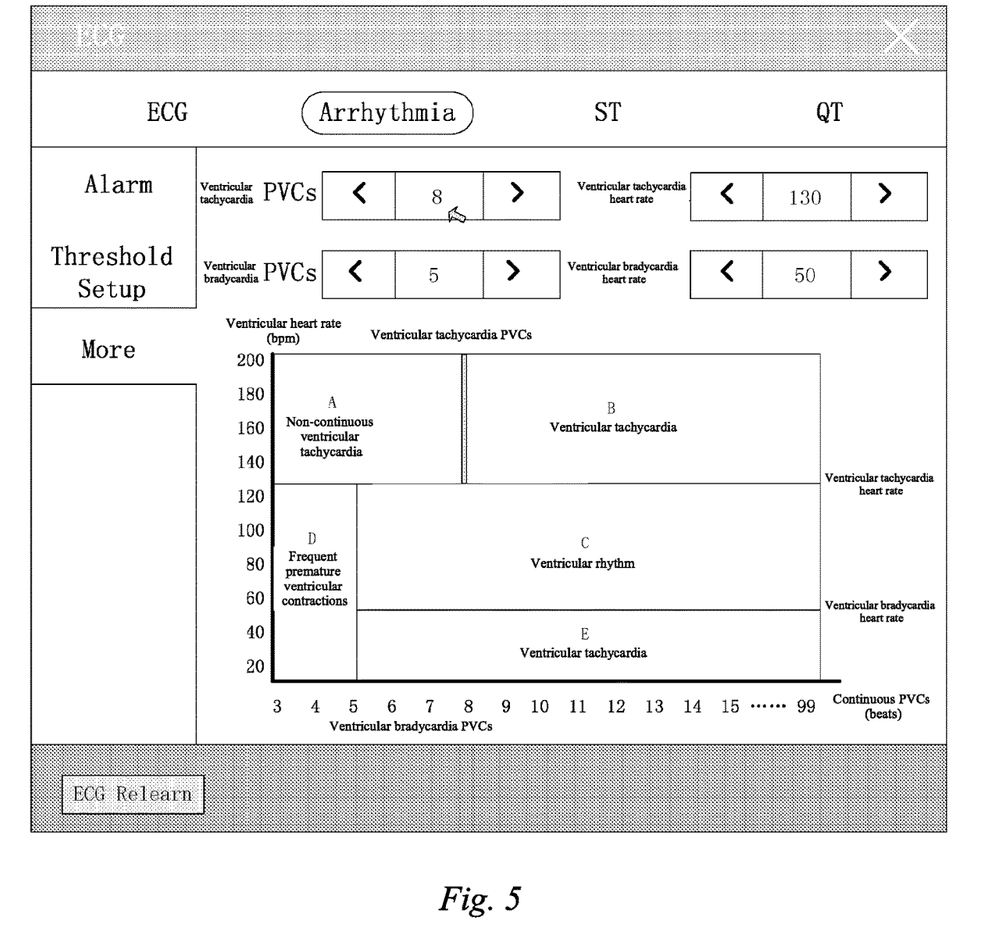
FIG. 5 is a schematic diagram of an interface after a threshold of an arrhythmia-related monitoring parameter is adjusted in FIG. 4.

Referring to FIG. 4 and FIG. 5, an example for setting thresholds of arrhythmia-related monitoring parameters by applying a monitoring parameter threshold setting method provided by the present disclosure is shown.

Threshold indicators of the arrhythmia-related monitoring parameters include ventricular tachycardia PVCs, ventricular bradycardia PVCs, a ventricular tachycardia heart rate, a ventricular bradycardia heart rate, and other threshold indicators. There is an association relationship of threshold indicator settings of these parameters. PVCs refers to premature ventricular contractions, and the PVCs refer to the number of premature ventricular contractions.

It can be seen from the schematic diagram of an interface shown in FIG. 4 that one or more threshold setting regions may be set for each monitoring parameter, and the size of a threshold of the monitoring parameter can be adjusted by arrows on both sides. If there is only a single threshold indicator for a single monitoring parameter, one threshold setting region may be correspondingly set. If there are two threshold indicators for a single monitoring parameter, two threshold setting regions may be set, and if there are more threshold indicators, more threshold setting regions may be set. In some embodiments, it is also possible to input a threshold of a monitoring parameter directly by using a hardware keyboard or a virtual keyboard. The monitoring parameter referred to herein may be a direct parameter value measured directly from a patient, or may be an indirect parameter calculated or analyzed based on a measured signal.

Furthermore, a two-dimensional threshold setting indication graph may be displayed on the interface. In the threshold setting indication graph, one of multiple measurement units corresponding to the multiple threshold indicators of the monitoring parameters, that is, a ventricular heart rate (bpm), is selected as an ordinate, and it is determined that a maximum value of the ordinate is 200, and another one of the multiple measurement units, that is, continuous PVCs (beats), is selected as an abscissa, and it is determined that a maximum value of the abscissa is 99.

In the threshold setting indication graph, a corresponding indication icon is set for each monitoring parameter threshold indicator. These indication icons may be in the form of segments or cursors parallel to the abscissa or the ordinate. Specifically, for the parameter PVCs, the parameter has two settable thresholds: a ventricular tachycardia PVCs threshold and a ventricular bradycardia PVCs threshold. Similarly, the heart rate also has two settable thresholds: a ventricular tachycardia heart rate threshold and a ventricular bradycardia heart rate threshold. Indication icons corresponding to the ventricular tachycardia PVCs and the ventricular bradycardia PVCs are segments parallel to the ordinate and are also segments perpendicular to the PVCs axis. Indication icons corresponding to the ventricular tachycardia heart rate and the ventricular bradycardia heart rate are segments parallel to the abscissa and are also segments perpendicular to the heart rate axis. These segments divide a region defined by the abscissa, an abscissa maximum value line, the ordinate, and an ordinate maximum value line (that is, a region determined by the PVCs axis and the heart rate axis and their respective maximum values), and expected analysis result information is displayed in each small region obtained after division. Specifically, the enclosed region is divided into several small regions such as A, B, C, D, and E, and the expected analysis result information is displayed in these small regions. For example, when data monitored by a monitor falls into the region E, that is, a measured ventricular heart rate is below 50 and continuous PVCs are over 5 cycles, it indicates that a patient under testing may suffer ventricular bradycardia.

In a specific example, the process of dividing the enclosed region into small regions may be implemented by using the following method. First, a certain number of horizontal lines are intersected with vertical lines to preliminarily divide the entire region, for example, two horizontal lines are intersected with two vertical lines to divide the region into nine sub-regions. Then, it is confirmed whether some of the sub-regions need to be merged according to an analysis criterion, and if necessary, corresponding merging is performed. Therefore, in FIG. 4, the region is finally divided into five sub-regions: A, B, C, D, and E according to a diagnostic criterion. It can be understood that, for different application scenarios, the number of sub-regions that are finally obtained by division and the size of each sub-region need to be comprehensively determined in combination with a diagnostic criterion and the number of parameters (dimensions).

In this way, when the user sets thresholds of the monitoring parameters, the relationship between the thresholds of the threshold indicators of the monitoring parameters can be intuitively seen from the threshold setting indication graph, so as to guide the user to accurately set the thresholds of the monitoring parameters.

Furthermore, to facilitate more intuitive use by the user, when the user operates a threshold indicator of a monitoring parameter, for example, when the user places a mouse cursor in a ventricular tachycardia PVCs threshold setting region, in the threshold setting indication graph, an indicator icon (segment) corresponding to the ventricular tachycardia PVCs is highlighted as a bold segment in the graph, so that the user can easily learn a corresponding position in the threshold setting indication graph of a threshold of the ventricular tachycardia PVCs currently set. It can be understood that, in practical applications, an indicator icon may also be highlighted in other ways according to needs, such as changing a color or flickering.

Similarly, it can be understood that, in some other implementations, a threshold setting region may also not be deployed in FIG. 4, but corresponding thresholds are indicated in indication icons in the threshold setting indication graph, and an indication icon (segment) may be dragged using a mouse, so as to adjust a threshold of a corresponding threshold indicator.

Referring to FIG. 5, there is shown a schematic diagram of an interface after a threshold of a threshold indicator of an arrhythmia-related monitoring parameter is adjusted in FIG. 4. In FIG. 5, the threshold of the ventricular tachycardia PVCs is adjusted from 6 to 8, and in the threshold setting indication graph, the indication icon (segment) corresponding to the ventricular tachycardia PVCs is adjusted to a position corresponding to an abscissa 8.

It can be understood that the adjustment of the indication icon may be displayed statically or dynamically.

For example, in one example, when the threshold of the ventricular tachycardia PVCs is adjusted to 8 in the threshold setting region, the corresponding indication icon is directly displayed at the position corresponding to the abscissa 8 in the threshold setting indication graph, and the indication icon is no longer displayed at a position corresponding to an abscissa 6.

In another example, when the threshold of the ventricular tachycardia PVCs is adjusted to 8 in the threshold setting region, in the threshold setting indication graph, the corresponding indication icon is dynamically moved (at a certain speed) from the position corresponding to the abscissa 6 to the position corresponding to the abscissa 8, and the moving process may be implemented by using, for example, an animation plug-in.

Figure 6:
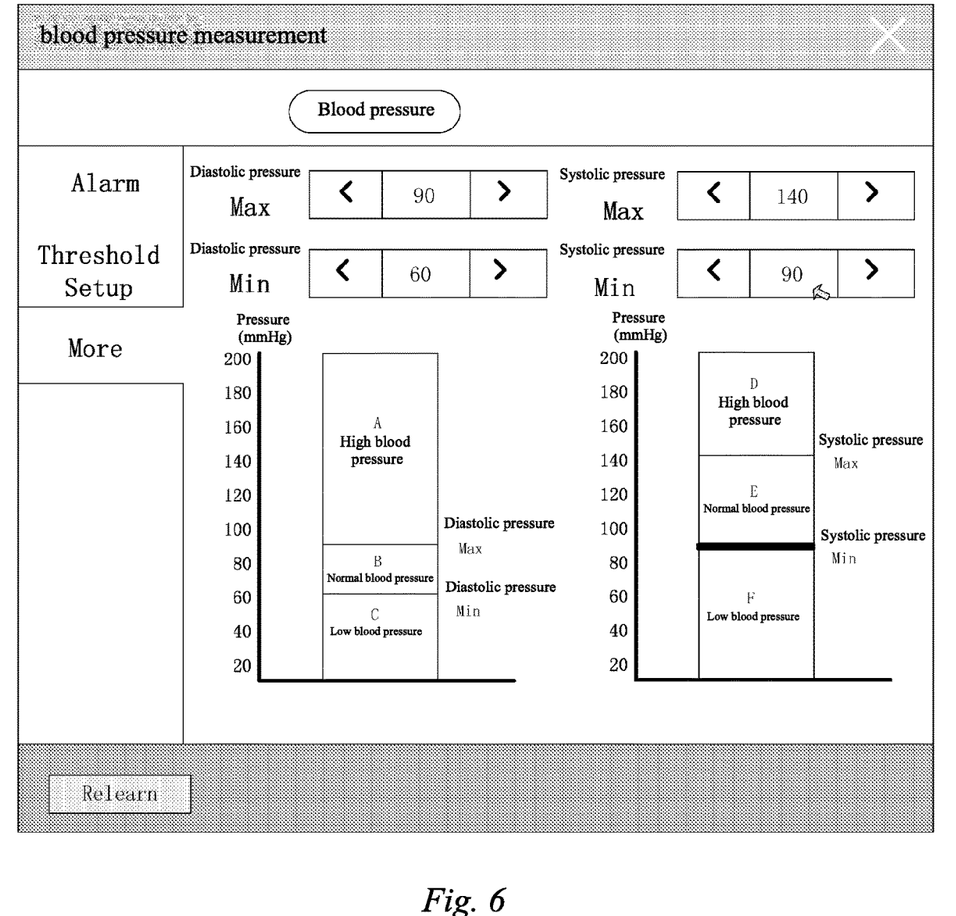
FIG. 6 is a schematic diagram of an interface for setting thresholds of blood pressure-related monitoring parameters by applying a monitoring parameter threshold setting method provided by the present disclosure.
Figure 7:
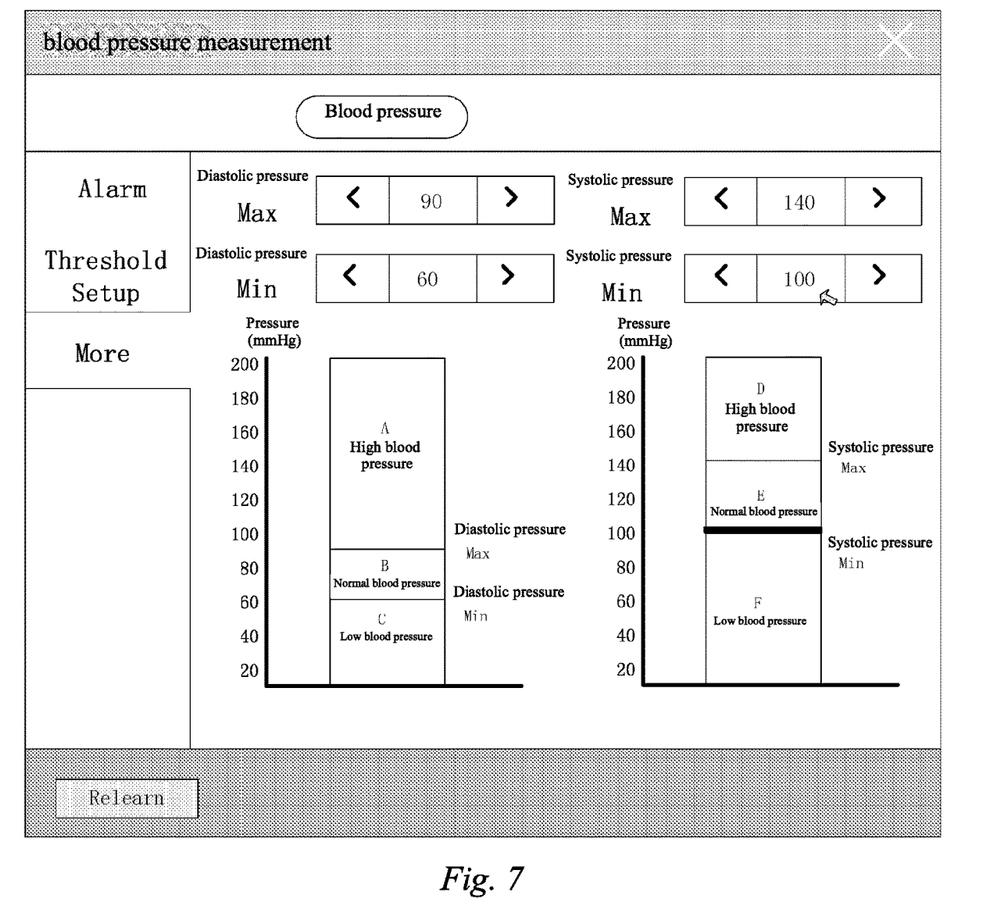
FIG. 7 is a schematic diagram of an interface after a blood pressure-related threshold is adjusted in FIG. 6.

Referring to FIG. 6 and FIG. 7, there is shown an example for setting thresholds of blood pressure-related monitoring parameters by applying a monitoring parameter threshold setting method provided by the present disclosure.

Referring to FIG. 6, threshold indicators of the blood pressure-related monitoring parameters include a maximum value (Max) of diastolic pressure, a minimum value (Min) of diastolic pressure, a maximum value (Max) of systolic pressure, a minimum value (Min) of systolic pressure, and the like. It can be seen from the schematic diagram of an interface shown in FIG. 6 that a threshold of a threshold indicator of each monitoring parameter may be set by using a threshold setting region. For example, the size of the threshold may be adjusted by using arrows on both sides. Certainly, other methods mentioned above in the description of FIG. 4 may also be used.

Furthermore, a two-dimensional threshold setting indication graph is displayed on the interface. In the threshold setting indication graph, a pressure (mmHg) in measurement units corresponding to the multiple threshold indicators of the monitoring parameters is selected as an ordinate, and it is determined that a maximum value of the ordinate is 200.

In the threshold setting indication graph, a corresponding indication icon is set for each monitoring parameter threshold indicator. These indication icons are segments parallel to an abscissa, and these segments divide a region defined by the abscissa, an abscissa maximum value line, a line parallel to the ordinate, and a line parallel to an ordinate maximum value line, and expected analysis result information is displayed in each small region obtained after division. Specifically, the enclosed region is divided into several small regions such as A, B, and C, and the expected analysis result information is displayed in these small regions. For example, when data monitored by a monitor falls into the region A, that is, a measured diastolic pressure is greater than 100, it indicates that a patient under test may suffer a high blood pressure.

In this way, when the user sets thresholds of the threshold indicators of the monitoring parameters, the relationship between the thresholds of the threshold indicators of the monitoring parameters can be intuitively seen from the threshold setting indication graph, so as to guide the user to accurately set the thresholds of the monitoring parameters.

Furthermore, to facilitate more intuitive use by the user, when the user operates a threshold indicator of a monitoring parameter, for example, when the user places a mouse cursor in a systolic pressure Min threshold setting region, in the threshold setting indication graph, an indicator icon (segment) corresponding to the systolic pressure Min is highlighted as a bold segment in the graph, so that the user can easily learn a corresponding position in the threshold setting indication graph of the systolic pressure Min currently set.

Similarly, for various possible variations of the threshold setting indication graph in FIG. 6, reference may be made to the foregoing description of FIG. 4, the details of which are not repeated here.

As shown in FIG. 7, a schematic diagram of an interface after a threshold of a threshold indicator of a blood pressure-related monitoring parameter is adjusted in FIG. 6 is shown. In FIG. 7, the threshold of the systolic pressure Min is adjusted from 90 in FIGS. 6 to 100, and in the setting indication graph, the indication icon (segment) corresponding to the systolic pressure Min is adjusted to a position corresponding to an ordinate 100.

In other examples, in the threshold setting indication graph in FIG. 6, the measurement unit pressure (mmHg) corresponding to the multiple threshold indicators of the monitoring parameters may also be selected as the abscissa, and the object of the present disclosure can also be achieved using a similar principle.

Figure 8:
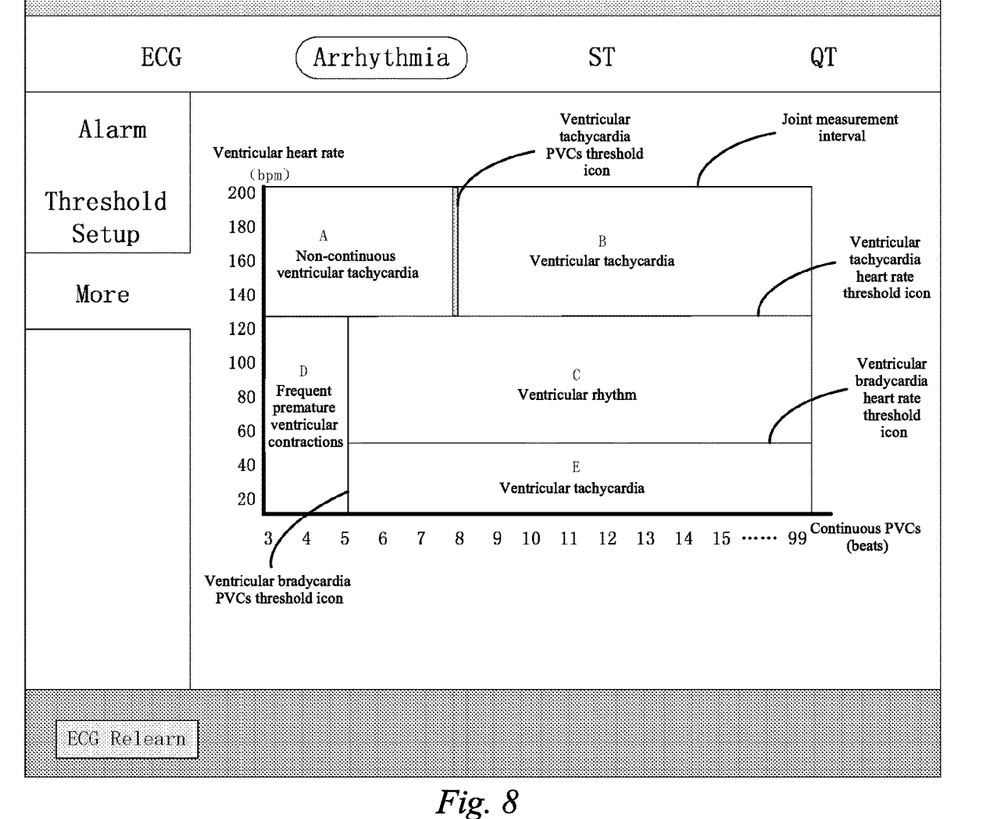
FIG. 8 is a schematic diagram of an interface for setting thresholds of arrhythmia-related monitoring parameters in another embodiment of the present disclosure.

In another embodiment of the present disclosure, as shown in FIG. 8, the arrhythmia-related threshold setting interface is a graphical threshold setting interface, and the graphical threshold setting interface is based on a two-dimensional coordinate system. A horizontal axis represents a value of a first monitoring parameter and a vertical axis represents a value of a second monitoring parameter, where the first monitoring parameter is a parameter continuous PVCs and the second monitoring parameter is a ventricular heart rate (or heart rate). The horizontal axis and the vertical axis are respectively cut off by maximum values of the corresponding monitoring parameters, and multiple values may be respectively displayed on the horizontal axis and the vertical axis. Steps of the numerical values may be set according to needs, for example, the values may be displayed in equal differences, or may be displayed with jumps. According to the horizontal axis, the vertical axis, a maximum value in the horizontal axis, and a maximum value in the vertical axis, a rectangular region may be formed, representing a joint measurement interval or a joint effective measurement interval.

For a first monitoring parameter, it has two adjustable thresholds, which are respectively defined as a first threshold and a second threshold. Specifically, the first threshold and the second threshold are respectively a ventricular tachycardia PVCs threshold and a ventricular bradycardia PVCs threshold. For a second monitoring parameter, it also has two adjustable thresholds, which are respectively defined as a third threshold and a fourth threshold. Specifically, the third threshold and the fourth threshold are respectively a ventricular tachycardia heart rate threshold and a ventricular bradycardia heart rate threshold. In the present disclosure, because different thresholds may be derived from a monitoring parameter according to diagnostic needs, sometimes the monitoring parameter is not divided into such fixed states as high and low or normal/abnormal according to measured values, but threshold indicators with specific meanings, such as ventricular tachycardia PVCs, ventricular bradycardia PVCs, a ventricular tachycardia heart rate, and a ventricular bradycardia heart rate are derived in combination with a diagnostic function. Certainly, this embodiment can also be applied to the case of a simple division of thresholds.

In the embodiment shown in FIG. 8, the first threshold, the second threshold, the third threshold, and the fourth threshold respectively correspond to a threshold icon (which may be respectively referred to as a first threshold icon, a second threshold icon, a third threshold icon, and a fourth threshold icon). Specifically, in this embodiment, the threshold icons are a ventricular tachycardia PVCs threshold icon, a ventricular bradycardia PVCs threshold icon, a ventricular tachycardia heart rate threshold icon, and a ventricular bradycardia heart rate threshold icon respectively. The ventricular tachycardia PVCs threshold icon and the ventricular bradycardia PVCs threshold icon are segments parallel to each other and parallel to the longitudinal axis. The ventricular tachycardia heart rate threshold icon and the ventricular bradycardia heart rate are segments parallel to each other and parallel to the horizontal axis. In this way, the above four threshold icons divide the joint measurement interval into several analysis result intervals, such as non-continuous ventricular tachycardia region (A), a ventricular tachycardia region (B), and a ventricular rhythm region (C). Assuming that the number of settable thresholds of the first monitoring parameter is m, the number of settable thresholds of the second monitoring parameter is n, and the number of analysis result intervals is Q. In the embodiment shown in FIG. 8, m=2, n=2, and Q<(m+1)*(n+1). For setting of thresholds of some other monitoring parameters, Q may be equal to (m+1)*(n+1).

After the thresholds are determined, the ventricular tachycardia PVCs threshold icon, the ventricular bradycardia PVCs threshold icon, the ventricular tachycardia heart rate threshold icon, and the ventricular bradycardia heart rate threshold icon remain at the corresponding threshold values respectively. When a user needs to adjust one or more of these thresholds (threshold indicators), a corresponding change can be made by moving, dragging, or sliding a corresponding threshold icon. When a threshold icon is selected, the threshold icon produces a visual effect different from the other threshold icons to prompt the user that moving the current threshold icon will change its threshold setting. As shown in FIG. 8, when the ventricular tachycardia PVCs threshold icon is selected, its threshold icon (segment) becomes thicker. During movement, the user can determine a current threshold value according to a corresponding value in the horizontal axis. In some other embodiments, when one threshold icon is selected, the threshold icon may also be distinguished from the threshold icons that are not currently selected by flickering, changing a color, changing to a dashed line, or the like. The current threshold may also be directly displayed near the threshold icon.

The above method can be applied to a single-parameter graphical threshold setting interface (such as one-dimensional coordinates), three-parameter graphical threshold setting interface (such as three-dimensional coordinates).

Figure 9:
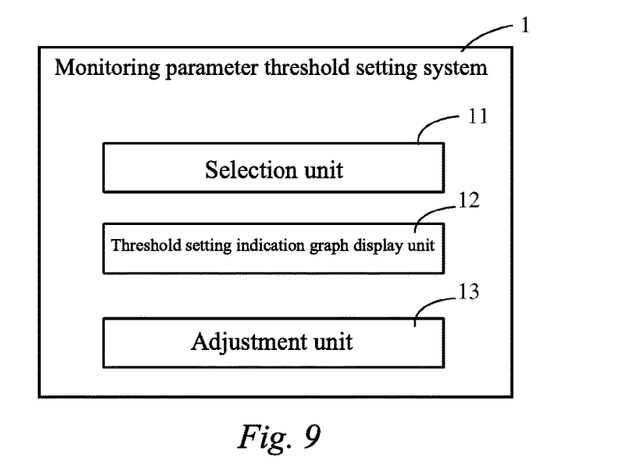
FIG. 9 is a schematic structural diagram of an embodiment of a system for setting a threshold of a monitoring parameter provided by the present disclosure.

Shown in FIG. 9 is a schematic structural diagram of an embodiment of a system for setting a threshold of a monitoring parameter provided by the present disclosure. In this embodiment, the system 1 for setting a threshold of a monitoring parameter specifically includes:

a selection unit 11 configured to allow a user to select at least one threshold indicator that is of a monitoring parameter and for which a threshold needs to be set;

a threshold setting indication graph display unit 12 configured to form and display a corresponding threshold setting indication graph according to the at least one threshold indicator of the monitoring parameter, where each threshold indicator of the monitoring parameter corresponds to an indication icon in the threshold setting indication graph, and the indication icon may be a segment or a cursor; and an adjustment unit 13 configured to adjust the indication icon corresponding to the threshold indicator of the monitoring parameter in the threshold setting indication graph to a corresponding position in response to setting a threshold value of each threshold indicator of the monitoring parameter by a user.

Specifically, the selection unit 11 may select a threshold indicator of the monitoring parameter and a threshold by using a threshold setting region, or may directly select an indication icon in the threshold setting indication graph displayed by the threshold setting indication graph display unit 12, to select a threshold indicator of the monitoring parameter for which a threshold needs to be set. For example, the threshold indicator of the monitoring parameter that needs to be set may be selected directly by selecting a horizontal line or a vertical line in the threshold setting indication graph, and the threshold of the corresponding threshold indicator of the monitoring parameter may be adjusted by moving a position of the horizontal line or the vertical line. For specific forms and functions of the threshold setting region and the threshold setting indication graph, reference may be made to the description of FIG. 4.

Specifically, in one example, the threshold setting indication graph display unit 12 is further configured to:

if two or more measurement units correspond to the at least one threshold indicator of the monitoring parameter, form and display a two-dimensional threshold setting indication graph according to an association relationship of the at least one threshold indicator of the monitoring parameter, where one of the measurement units is selected as an ordinate and a maximum value of the ordinate is determined, and another one of the measurement units is selected as an abscissa and a maximum value of the abscissa is determined; and an indication icon corresponding to each threshold indicator of the monitoring parameter is a segment parallel to the abscissa or the ordinate, and the at least one segment divides a region jointly enclosed by the abscissa, an abscissa maximum value line, the ordinate, and an ordinate maximum value line, and expected analysis result information is displayed in each small region obtained after division.

In this example, the threshold indicator of the monitoring parameters may include: a ventricular tachycardia PVCs threshold, a ventricular bradycardia PVCs threshold, a ventricular tachycardia heart rate threshold, and a ventricular bradycardia heart rate threshold, and a measurement unit of the ventricular tachycardia PVCs threshold is used as the abscissa, and a measurement unit of the ventricular tachycardia heart rate threshold is used as the ordinate.

In addition, in another example, the threshold setting indication graph display unit 12 is further configured to:

if one measurement unit corresponds to the at least one threshold indicator of the monitoring parameter, form and display a two-dimensional threshold setting indication graph according to an association relationship of the at least one threshold indicator of the monitoring parameter, where the measurement unit corresponding to the at least one threshold indicator of the monitoring parameter is selected as an ordinate, and a maximum value of the ordinate is determined; and an indication icon corresponding to each threshold indicator of the monitoring parameter is parallel to an abscissa, and at least one segment divides a region jointly enclosed by the ordinate or a line parallel to the ordinate, an ordinate maximum value line or a line parallel to the ordinate maximum value line, and the abscissa, and expected analysis result information is displayed in each small region obtained after division.

Figure 10:
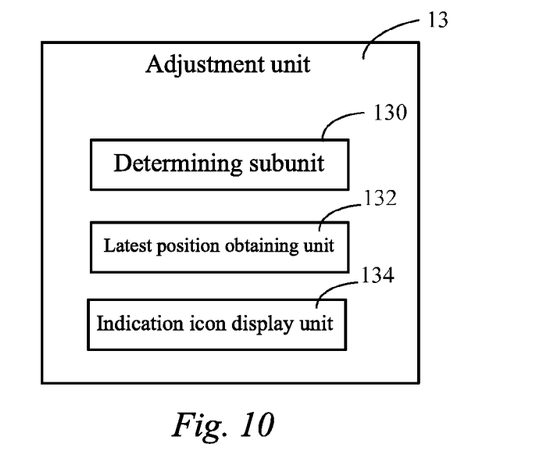
FIG. 10 is a schematic structural diagram of an embodiment of an adjustment unit in FIG. 9.

In FIG. 10, there is shown a schematic structural diagram of an embodiment of the adjustment unit in FIG. 9. In this embodiment, the adjustment unit 13 further includes:

a determining subunit 130 configured to determine a threshold indicator of the monitoring parameter that is currently operated by the user, and an indication icon corresponding to the threshold indicator of the monitoring parameter;

a latest position obtaining unit 132 configured to obtain a latest position of the indication icon corresponding to the threshold indicator according to a latest threshold value set by the user for the threshold indicator; and an indication icon display unit 134 configured to display the indication icon at the latest position in the threshold setting indication graph.

Figure 11:
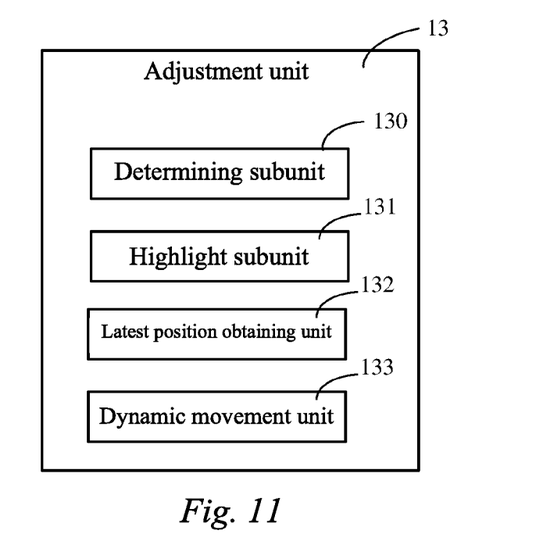
FIG. 11 is a schematic structural diagram of another embodiment of the adjustment unit in FIG. 9.

Referring to FIG. 11, a structural schematic diagram of another embodiment of the adjustment unit in FIG. 9 is shown. In this embodiment, the adjustment unit 13 further includes:

a determining subunit 130 configured to determine a threshold indicator of the monitoring parameter that is currently operated by the user, and an indication icon corresponding to the threshold indicator of the monitoring parameter;

a highlight subunit 131 configured to highlight the indication icon corresponding to the threshold indicator of the monitoring parameter operated by the user in the threshold setting indication graph, where the highlight subunit highlights the indicator icon by flickering, color changing, or thickness changing;

a latest position obtaining unit 132 configured to obtain a latest position of the indication icon corresponding to the threshold indicator according to a latest threshold value set by the user for the threshold indicator; and a dynamic movement unit 133, configured to dynamically move the indication icon from a current position to the latest position in the threshold setting indication graph.

The present disclosure further provides a monitor, which includes at least the system for setting a threshold of a monitoring parameter described above in combination with FIGS. 9-11. For more details, reference may be made to the foregoing description of FIGS. 9-11, which are not repeated here.

It can be understood that the above embodiments in the method, the system, and the monitor are all examples. In other applications, if three or more measurement units correspond to multiple threshold indicators of a monitoring parameter, a threshold setting indicator graph having more dimensions may also be used. For example, in some examples, if three measurement units correspond to multiple threshold indicators of a monitoring parameter, each measurement unit may be used as a coordinate to form a three-dimensional threshold setting indication graph.

Finally, by implementing the method and system provided by the embodiments of the present disclosure, the following beneficial effects can be achieved. First, by implementing the embodiments of the present disclosure, when a user sets a threshold of at least one threshold indicator of a monitoring parameter, a preset threshold setting indication graph can be used to indicate a relationship between thresholds of the threshold indicators of the monitoring parameter.

Furthermore, a threshold indicator of the monitoring parameter that is being set is highlighted, different from the other threshold indicators of the monitoring parameter.

Moreover, when a threshold value of a threshold indicator of the monitoring parameter is adjusted, a graphical change corresponding to the threshold of the threshold indicator of the monitoring parameter is displayed in the threshold setting indication graph.

Therefore, by implementing the embodiments of the present disclosure, when a user sets a threshold of a monitoring parameter, graphical indications can be realized, so as to improve the accuracy of threshold setting.

It may be understood by those skilled in the art that all or part of the processes for implementing the method in the foregoing embodiments may be implemented by a computer program instructing relevant hardware. The program may be stored in a non-transitory computer-readable storage medium. A processor may execute the program to perform the methods described herein. The storage medium may be a magnetic disk, an optical disk, a read-only memory (ROM), a random access memory (RAM), or the like.

The technical features or operation steps described in the embodiments of the present disclosure may be combined in any suitable manner. Those skilled in the art can easily understand that the order of the steps or actions in the method described in the embodiments of the present disclosure may be changed. Therefore, unless a specific order is required otherwise, any order shown in the drawings or detailed description is for illustrative purposes only, and is not a necessary order.

Disclosed above is merely examples of presently preferred embodiments of the present disclosure and certainly cannot be used to limit the scope of the present disclosure. Therefore, equivalent changes made according to the claims of the present disclosure are still covered by the present disclosure.

What is claimed is:

1. A method performed by a patient monitor for setting at least one alarm for a patient condition, comprising:

receiving, by an input of the patient monitor, a user operation of at least one threshold indicator from threshold indicators of a first monitoring parameter and a second monitoring parameter;

displaying, on a display of the patient monitor, a threshold setting indication graph according to threshold indicators of the first monitoring parameter and the second monitoring parameter, wherein one threshold indicator corresponds to an indication icon in the threshold setting indication graph; and in response to a threshold value of one threshold indicator from the at least one threshold indicator of the user operation, adjusting an indication icon corresponding to said one threshold indicator in the threshold setting indication graph to a corresponding position, wherein the threshold indicator of the first monitoring parameter corresponds to a first measurement unit, and the threshold indicator of the second monitoring parameter corresponds to a second measurement unit;

wherein displaying the threshold setting indication graph comprises displaying a two-dimensional threshold setting indication graph according to an association relationship between the threshold indicator of the first monitoring parameter and the threshold indicator of the second monitoring parameter, wherein the first measurement unit is selected as the ordinate with a pre-set maximum value, the second measurement unit is selected as the abscissa with a pre-set maximum value, the indication icon corresponding to the threshold indicator of the first monitoring parameter is a line segment parallel to the abscissa, the indication icon corresponding to the threshold indicator of the second monitoring parameter is a line segment parallel to the ordinate, the line segment parallel to the abscissa and the line segment parallel to the ordinate divide a region enclosed by an abscissa maximum value line, the abscissa, the ordinate, and an ordinate maximum value line to sub-regions, and each divided sub-region displays expected analysis result information; and setting an alarm in the patient monitor corresponding to the threshold indicator of the first monitoring parameter and the threshold indicator of the second monitoring parameter represented in the threshold setting indication graph, wherein the patient monitor signals the alarm in response to monitoring measured values of the first monitoring parameter and the second monitoring parameter, wherein the monitoring parameter comprises premature ventricular contractions (PVCs) and a heart rate, the PVCs correspond to two threshold indicators: ventricular tachycardia PVCs and ventricular bradycardia PVCs, and the heart rate corresponds to two threshold indicators: a ventricular tachycardia heart rate and a ventricular bradycardia heart rate, wherein a PVCs measurement unit is selected as the abscissa and a heart rate measurement unit is selected as the ordinate.

2. The method of claim 1, wherein adjusting further comprises:
   determining a threshold indicator of the monitoring parameter that is currently operated by the user, and an indication icon corresponding to the threshold indicator; the operated threshold indicator is the threshold indicator of the first monitoring parameter or the second monitoring parameter;
   obtaining a latest position of the indication icon corresponding to the threshold indicator according to a latest threshold value set by the user for the threshold indicator; and
   adjusting the indication icon to the latest position in the threshold setting indication graph.

3. The method of claim 1, wherein an indication icon corresponding to ventricular tachycardia PVCs is a first adjustable segment parallel to the ordinate, the indication icon corresponding to ventricular bradycardia PVCs is a second adjustable segment parallel to the ordinate, and the first adjustable segment and the second adjustable segment are parallel to each other; the indication icon corresponding to ventricular tachycardia heart rate is a third adjustable segment parallel to the abscissa, the indication icon corresponding to ventricular bradycardia heart rate is a fourth adjustable segment parallel to the abscissa, and the third adjustable segment and the fourth adjustable segment are parallel to each other.

4. The method of claim 1, wherein the input of the patient monitor includes a hardware keyboard or a virtual keyboard.

5. The method of claim 1, wherein each sub-region is obtained by dividing the threshold setting indication graph into sub-regions through multiple horizontal and vertical lines, and merging the sub-regions according to analysis criteria.

6. The method of claim 5, wherein there are five divided sub-regions.

7. The method of claim 6, wherein a threshold of an indication icon is displayed near the indication icon.

8. The method of claim 1, wherein the input of the patient monitor is a drag operation for the indication icon, and
   wherein adjusting the indication icon corresponding to the threshold indicator in the threshold setting indication graph to a corresponding position comprises:
      moving the indication icon corresponding to the threshold indicator in the threshold setting indication graph to a corresponding position according to the drag operation.

9. The method of claim 8, wherein the adjusting comprises using flickering, color change or thickness change to highlight the indication icon when dragged.

10. The method of claim 8, wherein a dragging process of the drag operation is displayed through an animation plug-in.

11. The method of claim 1, wherein adjusting further comprises:
    determining a threshold indicator of the monitoring parameter that is currently operated by the user, and an indication icon corresponding to the threshold indicator;
    the operated threshold indicator is the threshold indicator of the first monitoring parameter or the second monitoring parameter;
    highlighting the indication icon corresponding to the threshold indicator operated by the user in the threshold setting indication graph;
    obtaining a latest position of the indication icon corresponding to the threshold indicator according to a latest threshold value set by the user for the threshold indicator of the monitoring parameter; and
    dynamically moving the indication icon from a current position to the latest position in the threshold setting indication graph.

12. The method of claim 11, wherein highlighting comprises highlighting the indication icon by flickering, color changing, or thickness changing.

13. A method performed by a patient monitor for setting at least one alarm for a patient condition, comprising:
    receiving, by an input of the patient monitor, an adjustment of a threshold value for each threshold indicator of at least one threshold indicator from threshold indicators of a first monitoring parameter and a second monitoring parameter by a user, and a threshold value of each threshold indicator can be adjusted by arrows on both sides;
    displaying, on a display of the patient monitor, a threshold setting indication graph according to threshold indicators of the first monitoring parameter and the second monitoring parameter, wherein one threshold indicator corresponds to an indication icon in the threshold setting indication graph; and in response to the adjustment of a threshold value of one threshold indicator from the at least one threshold indicator, adjusting an indication icon corresponding to said one threshold indicator in the threshold setting indication graph to a corresponding position, wherein the threshold indicator of the first monitoring parameter corresponds to a first measurement unit, and the threshold indicator of the second monitoring parameter corresponds to a second measurement unit;

wherein displaying the threshold setting indication graph comprises displaying a two-dimensional threshold setting indication graph according to an association relationship between the threshold indicator of the first monitoring parameter and the threshold indicator of the second monitoring parameter, wherein the first measurement unit is selected as the ordinate with a pre-set maximum value, the second measurement unit is selected as the abscissa with a pre-set maximum value, the indication icon corresponding to the threshold indicator of the first monitoring parameter is a line segment parallel to the abscissa, the indication icon corresponding to the threshold indicator of the second monitoring parameter is a line segment parallel to the ordinate, the line segment parallel to the abscissa and the line segment parallel to the ordinate divide a region enclosed by an abscissa maximum value line, the abscissa, the ordinate, and an ordinate maximum value line to sub-regions, and each divided sub-region displays expected analysis result information; and setting an alarm in the patient monitor corresponding to the threshold indicator of the first monitoring parameter and the threshold indicator of the second monitoring parameter represented in the threshold setting indication graph, wherein the patient monitor signals the alarm in response to monitoring measured values of the first monitoring parameter and the second monitoring parameter, wherein the monitoring parameter comprises premature ventricular contractions (PVCs) and a heart rate, the PVCs correspond to two threshold indicators: ventricular tachycardia PVCs and ventricular bradycardia PVCs, and the heart rate corresponds to two threshold indicators: a ventricular tachycardia heart rate and a ventricular bradycardia heart rate, wherein a PVCs measurement unit is selected as the abscissa and a heart rate measurement unit is selected as the ordinate.

14. The method of claim 13, wherein the input of the patient monitor includes a hardware keyboard or a virtual keyboard.

15. The method of claim 13, wherein each sub-region is obtained by dividing the threshold setting indication graph into sub-regions through multiple horizontal and vertical lines, and merging the sub-regions according to analysis criteria.

16. The method of claim 15, wherein there are five divided sub-regions.

17. A method performed by a patient monitor for setting at least one alarm for a patient condition, comprising:

receiving, by an input of the patient monitor, a drag operation or a slide operation for an indication icon of each threshold indicator of at least one threshold indicator from threshold indicators of a first monitoring parameter and a second monitoring parameter;

displaying, on a display of the patient monitor, a threshold setting indication graph according to threshold indicators of the first monitoring parameter and the second monitoring parameter, wherein one threshold indicator corresponds to an indication icon in the threshold setting indication graph; and in response to the drag operation or the slide operation, moving the indication icon corresponding to the threshold indicator in the threshold setting indication graph to a corresponding position, wherein the threshold indicator of the first monitoring parameter corresponds to a first measurement unit, and the threshold indicator of the second monitoring parameter corresponds to a second measurement unit;

wherein displaying the threshold setting indication graph comprises displaying a two-dimensional threshold setting indication graph according to an association relationship between the threshold indicator of the first monitoring parameter and the threshold indicator of the second monitoring parameter, wherein the first measurement unit is selected as the ordinate with a pre-set maximum value, the second measurement unit is selected as the abscissa with a pre-set maximum value, the indication icon corresponding to the threshold indicator of the first monitoring parameter is a line segment parallel to the abscissa, the indication icon corresponding to the threshold indicator of the second monitoring parameter is a line segment parallel to the ordinate, the line segment parallel to the abscissa and the line segment parallel to the ordinate divide a region enclosed by an abscissa maximum value line, the abscissa, the ordinate, and an ordinate maximum value line to sub-regions, and each divided sub-region displays expected analysis result information; and setting an alarm in the patient monitor corresponding to the threshold indicator of the first monitoring parameter and the threshold indicator of the second monitoring parameter represented in the threshold setting indication graph, wherein the patient monitor signals the alarm in response to monitoring measured values of the first monitoring parameter and the second monitoring parameter, wherein the monitoring parameter comprises premature ventricular contractions (PVCs) and a heart rate, the PVCs correspond to two threshold indicators: ventricular tachycardia PVCs and ventricular bradycardia PVCs, and the heart rate corresponds to two threshold indicators: a ventricular tachycardia heart rate and a ventricular bradycardia heart rate, wherein a PVCs measurement unit is selected as the abscissa and a heart rate measurement unit is selected as the ordinate.

18. The method of claim 17, wherein the adjusting comprises using flickering, color change or thickness change to highlight the indication icon when dragged.

19. The method of claim 17, wherein a dragging process of the drag operation is displayed through an animation plug-in.

20. The method of claim 17, wherein a threshold of an indication icon is displayed near the indication icon.

* * * * *